United States Patent [19]
Cuca et al.

[11] Patent Number: 5,554,380
[45] Date of Patent: Sep. 10, 1996

[54] BIOADHESIVE PHARMACEUTICAL DELIVERY SYSTEM

[75] Inventors: Robert C. Cuca, Edwardsville, Ill.; Keith S. Lienhop, St. Charles, Mo.; Thomas C. Riley, Jr., Ballwin, Mo.; R. Saul Levinson, Chesterfield, Mo.; Mitchell I. Kirschner, St. Louis, Mo.

[73] Assignee: KV Pharmaceutical Company, St. Louis, Mo.

[21] Appl. No.: 441,297

[22] Filed: May 15, 1995

Related U.S. Application Data

[63] Continuation-in-part of Ser. No. 283,904, Aug. 4, 1994, abandoned.

[51] Int. Cl.$^6$ .............................. A61K 9/28; A61K 9/68; A61K 9/20
[52] U.S. Cl. .......................... 424/441; 424/439; 424/440; 424/464; 424/465
[58] Field of Search .................. 514/772.2; 424/439, 424/440, 441, 464, 465

[56] References Cited

U.S. PATENT DOCUMENTS

| | | | |
|---|---|---|---|
| 4,011,661 | 3/1977 | Sezaki et al. | 34/9 |
| 4,040,857 | 8/1977 | Lissant | 106/243 |
| 4,184,978 | 1/1980 | France et al. | 252/309 |
| 4,280,996 | 7/1981 | Okamoto et al. | 252/316 |
| 4,340,594 | 7/1982 | Mizushima et al. | 424/238 |
| 4,385,049 | 5/1983 | Cuca | 424/168 |
| 4,439,194 | 3/1984 | Harwood et al. | 604/890 |
| 4,542,020 | 9/1985 | Jackson et al. | 514/781 |
| 4,551,148 | 11/1985 | Riley, Jr. et al. | 604/890.1 |
| 4,606,913 | 8/1986 | Aronson et al. | 424/59 |
| 4,698,359 | 10/1987 | Niederer et al. | 514/966 |
| 4,720,353 | 1/1988 | Bell | 252/309 |
| 4,831,018 | 5/1989 | Kirsh et al. | 514/938 |
| 4,857,335 | 8/1989 | Bohm | 424/440 |
| 4,874,605 | 10/1989 | Urban, Jr. et al. | 514/944 |
| 4,882,160 | 11/1989 | Yang et al. | 424/440 |
| 4,891,208 | 1/1990 | Janoff et al. | 604/891.1 |
| 4,929,447 | 5/1990 | Yang | 424/440 |
| 4,960,764 | 10/1990 | Fignerao, Jr. et al. | 514/938 |
| 5,010,067 | 4/1991 | Handley et al. | 514/943 |
| 5,019,397 | 5/1991 | Wong et al. | 424/473 |
| 5,055,303 | 10/1991 | Riley, Jr. | 514/966 |
| 5,215,758 | 6/1993 | Krishnamurthy | 424/488 |

*Primary Examiner*—Carlos Azpuru
*Attorney, Agent, or Firm*—Nath & Associates; Gary M. Nath

[57] ABSTRACT

A solid or semi-solid bioadherent, orally ingestible drug delivery system containing a water-in-oil system having at least two phases, one phase comprises from about 25% to about 75% by volume of an internal hydrophilic phase and the other phase comprises from about 25% to about 75% by volume of an external hydrophobic phase and wherein the external hydrophobic phase is comprised of three components, a) an emulsifier, b) a glyceride ester and c) a wax material.

43 Claims, No Drawings

5,554,380

BIOADHESIVE PHARMACEUTICAL DELIVERY SYSTEM

PRIOR APPLICATION

This application is a Continuation-In-Part application of U.S. patent application Ser. No. 08/283,904, filed Aug. 4, 1994, now abandoned, the entire contents of which are incorporated by reference.

BACKGROUND OF THE INVENTION

1. Field of the Invention

This invention relates to stable solid or semi-solid water-in-oil emulsions that are usable as bioadherent, ingestible systems. The systems are designed to coat and adhere to the oral cavity, epithelial and mucosal membranes of the esophagus and gastrointestinal (GI) tract for extended periods of time. The purpose of the coating is to protect the mouth tissue and the membranes of the pharynx and the esophagus, while promoting healing and to enable release of active drug in a delayed release rate. Confectionery and chewing gum compositions containing the emulsions are also described.

2. Description of the Prior Art

Oral pharmaceutical formulations are administered to patients in many forms, such as liquid solutions, emulsions, or suspensions, as well as in solid forms such as capsules or tablets. Preparations administered in tablet or capsule form are usually intended to be swallowed whole. It is of significant advantage to both the patient and clinician that medication be formulated so that it may be administered in a minimum number of daily doses from which the drug is uniformly released over a desired extended period of time. Various techniques have been developed for the purpose of including a pharmaceutical preparation comprising a drug-containing particle with a coating layer and a pharmaceutical preparation comprising a continuous matrix with a drug dispersed therein, such as embedded into a rigid lattice of resinous material in order to control the release of drugs. Representative U.S. Patents covering this technology include the following patents:

U.S. Pat. No. 5,059,426 to Cherukuri et al. discloses a process for preparing a delivery system comprised of a zinc core material coated with a first hydrophilic coating comprising a hydrocolloid material and a second hydrophobic coating selected from the group consisting of fats, waxes and mixtures thereof. The delivery system masks the bitter flavor characteristic of zinc compounds.

U.S. Pat. No. 4,597,970 to Sharma et al. discloses a delivery system capable of effecting a controlled release of core material comprising: (a) at least one natural or artificial sweet material and (b) a hydrophobic matrix consisting essentially of (i) lecithin; and (ii) an edible material having a melting point in the range of about 25° C. to about 100° C. selected from the group consisting of (a) fatty acids having an iodine value of about 1 to about 10, (b) natural waxes, (c) synthetic waxes and (d) mixtures thereof; and (iii) at least one glyceride.

U.S. Pat. No. 4,695,467 to Uemura et al. relates to a sustained release tablet which comprises easily disintegratable granules containing (a) a drug, (b) a disintegrating agent selected from the group consisting of starch derivatives, gums, cellulose derivatives and ion-exchange resins, and (c) a water-soluble polymer selected from the group consisting of cellulose derivatives, synthetic water soluble polymers and polysaccharides, the surfaces of which granules are treated with a wax selected from the group consisting of plant or animal wax, hydrogenated oils and paraffin.

Other forms for delivering pharmaceutical agents include emulsions and suspensions. Although a need for water-in-oil emulsions having a high water or aqueous phase content has long existed for use in pharmaceutical preparations, such as night creams or barrier creams and lotions, it has been difficult to provide such emulsion where the aqueous phase exceeds 45% to 55% on a weight by weight basis. Although many benefits are to be derived from providing a high water content in a water-in-oil emulsion system for cosmetic applications in particular, formulators have not heretofore been able to add more than about 50% water to the emulsion without seriously affecting the shelf life stability of the preparation. It is to be appreciated in this respect that because of the time delay that occurs between formulation of a product and commercial sale, it is undesirable to employ an emulsion which will break in a short period of time, particularly when exposed to temperature extremes that are encountered during transportation and warehouse storage. Although stability under normal climatic conditions is an asset, at the very minimum the emulsion system should be able to withstand temperatures on the order of 43° C. (110° F.) for at least six months without breaking.

Water-in-oil- emulsions are used in barrier preparations or pore-occluding products to provide a thin oleaginous-layer over the areas of the user's skin to which the composition is applied. Increasing the amount of hydrophilic inner phase in the emulsion decreases the oily feel of the material without deleteriously effecting the overall utility of the formulation. Such formulations have greater customer appeal because the higher hydrophilic content enhances the evaporative and thereby cooling effect of the cream or lotion upon application. Products formulated from these emulsion systems are described in U.S. Pat. No. 4,385,049 to Robert C. Cuca.

The use of water-in-oil emulsions as a liquid or semi-liquid system for oral use have not been successful. U.S. Pat. No. 2,948,686 to Gianladis describes water-in-oil emulsions but the patentee was not able to incorporate more than about 52% water in the emulsion system.

The present invention overcomes these deficiencies by preparing an orally useable and stable solid or semi-solid emulsion or suspension having an internal hydrophilic phase with a multifunctional hydrophobic external phase containing at least three separate components, an emulsifier, a glyceride ester and a wax material. Such systems enable the inventive formulation, when taken orally to coat and protect the oral cavity, and membranes of the esophagus and pharynx while enabling an active drug to be released from the formulation in a delayed rate of release.

SUMMARY OF THE INVENTION

This invention relates to the preparation of a solid or semi-solid bioadherent, orally ingestible system, which comprise: a water-in-oil emulsion system having at least two phases, one phase comprises from about 25% to about 75% by volume of an internal hydrophilic phase and the other phase comprises from about 25% to about 75% by volume of an external hydrophobic phase, wherein the external hydrophobic phase is composed of three components, a) one component being about 5% to about 50% of an emulsifier, b) a second component being about 0% to about 75% of a mixture of glyceride esters of long chain fatty acids, and c) a third component being about 10% to about 50% of a wax material having a melting point within the range of about 50° C. to about 200° C.

In a preferred embodiment the hydrophilic phase contains an active pharmaceutical material which is water-soluble.

In another preferred embodiment, water-insoluble active pharmaceutical materials are used in the hydrophobic phase.

Additional preferred embodiments involve selecting the hydrophilic phase from water, glycerine, sorbitol solutions, sugar syrups, polymer solutions and mixtures thereof. In contrast, the hydrophobic phase contains glyceride esters selected from the group consisting of long chain fatty acids having from 12 to 32 carbon atoms.

The emulsion of the invention also contain emulsifiers. Preferably, the emulsifiers are soluble in the hydrophobic (lipoidal) or external phase. Suitable emulsifiers are those oil miscible surface active compounds which are acceptable for use in foods, pharmaceuticals, and/or cosmetics. Examples of such emulsifiers are low molecular weight polyglycerols which have been esterified with fatty acids or fatty acid esters, or mono and diglyceride mixtures alone or with the addition of metallic soaps, such as, aluminum stearate. The metallic soaps appear to improve the characteristics of some of the emulsion. Additional emulsifiers present in the hydrophobic phase may also be selected from the group consisting of sorbitan esters, lecithin, 1 to 5 mole ethoxylates of fatty acids or alcohols, saccharides derivatives and mixtures thereof.

In a further embodiment of the invention, a method is provided for treating an oral or esophageal disorder, or for providing for the absorption of an active material for a systemic effect in an animal which comprises administering to the oral cavity a therapeutically effective amount of a solid or semi-solid bioadherent, orally ingestible system, which comprises: a water-in-oil system having at least two phases, one phase comprises from about 25% to about 75% by volume of an internal hydrophilic phase the other phase comprises from about 25% to about 75% by volume of an external hydrophobic phase is comprised of at least three components, one component being about 5% to about 50% of an emulsifier, a second component being about 0% to about 75% of a mixture of glyceride esters of long chain fatty acids and a third component being about 10% to about 50% of a wax material having a melting point within the range of about 50° C. to about 200°.

In a further embodiment, a chewing gum composition is provided for delivering the emulsions of this invention to the oral cavity which comprises a medicated chewing gum composition, which comprises: a) a gum base in an amount sufficient to form a chewing gum composition; b) effective amount of chewing gum additives to soften the gum base; and, c) an effective amount of an active pharmaceutical composition dispersed within a water-in-oil emulsion system having at least two phases, one phase comprises from about 25% to 75% by volume of an internal hydrophilic phase and the other phase comprises from abut 25% to about 75% by volume of an external hydrophobic phase, wherein the external hydrophobic phase is comprised of three components, a) one component being about 5% to about 50% of an emulsifier, b) a second component being about 10% to about 75% of a mixture of glyceride esters of long chain fatty acids and c) a third component being about 10° to about 50° of a wax material.

In another embodiment, a confectionery composition is provided for delivering the emulsions of this invention to the oral cavity which comprises a medicated confectionery composition, which comprises: a) a confectionery composition; and, b) an effective amount of an active pharmaceutical composition dispersed within a water-in-oil emulsion system having at least two phases, one phase comprises from about 25% to about 75% by volume of an internal hydrophilic phase and the other phase comprises from about 25% to about 75% by volume of an external hydrophobic phase, wherein the external hydrophobic phase is comprised of three components, a) one component being about 5% to about 50% of an emulsifier, b) a second component being about 10 to about 75% of a mixture of glyceride esters of long chain fatty acids and c) a third component being about 10° to about 50° of a wax material.

DETAILED DESCRIPTION OF THE INVENTION

The present invention provides an orally useable emulsion or suspension in solid or semi-solid form. Preferably the system liquifies when taken orally at body temperatures and is taken orally for the purpose of coating the mouth cavity, esophageal, pharynx tissue and/or GI tract membranes. Alternatively, the emulsion is delivered in a suitable pharmaceutical carrier, chewing gum composition, confectionery composition, or other acceptable carrier vehicle.

When the emulsions are used directly or in a carrier, they are intended to remain in place for extended periods of time and can serve as a reservoir for the delivery of drug or pH modifying ingredients. The property common to all formulations of this invention is the coating and adhering of the system to mucosal membranes of the mouth, pharynx, esophagus and/or GI tract for extended periods of time, independent of the form in which they are delivered.

The formulations coat and protect membranes of the mouth, pharynx, esophagus and/or GI tract, while promoting healing of esophagitis and ulcers as well as other disorders. The resulting protective layer also has the potential to provide a reservoir of drugs or pH modifying ingredients.

The formulations may contain an extended release buffer for controlling pH over an extended period of time by prolonged stomach residence through adhesion to the esophagus and villi as well as through swelling and resisting pylorus dumping. In addition, the film layer, which is amorphous in structure when adhered to biological tissue, continually adjusts itself with organ musculature creating a symbiotic, therapeutic system residing for extended periods of time in the target issue, such as in the mouth, esophagus, pharynx and/or stomach. Because of the unique emulsion system, the protective film has the potential to increase in thickness as time goes on by absorption of resident fluids into the hydrophilic layer of the system. This can then provide a thicker layer as a protectant. In contrast, prior art polymer systems have the potential to wash away quickly.

As discussed, the bioadherent system of this invention is able to adhere to the mucosa for long periods of time. During adherence, the system absorbs moisture and enables the drug to be transported across the epithelial tissue. Adherence occurs for from 30 minutes to 24 hours and preferably 2 to 8 hours. it has been calculated that by using the system of this invention a diffusion matrix is formed which enables the transport of biologically active material from the system through the epithelial tissue in less than 2 hours and preferably from 50 minutes to 2 hours.

While not being bound by any particular theory of activity, it is believed that the present bioadhesion system enables sufficient active ingredient to diffuse from the BIOADHESIVE substrate through the oral or esophageal epithelium and through and into the vasculature of the capillary beds present within the oral and esophageal mucosa. These capillary beds have direct access to and are drained into the general systemic circulation of fluids within the body including plasma, serum, lymph and blood.

A distinct advantage of using a bioadhesive substrate on the oral and esophageal mucosa is to effect the systemic circulation of sufficient active agents resulting from an oral administration of the active agent/drug delivery system to the oral cavity and esophagus. In this manner, biologically sensitive material may be administered orally, which has not been possible heretofore.

In conventional treatments, biologically sensitive material, such as proteins and hormones are administered by direct injection or infusion directly into the systemic circulation because the active drug is essentially digested and destroyed after introduction to the gastrointestinal tract. In the present bioadhesive delivery systems, the active drug is delivered in a protected manner that is not hostile to the active drug and, yet, due to the bioadhesive nature of the drug delivery platform, allows sufficient retention time at the site of absorption for sufficient absorption of the active drug. Further, incorporation of the active drug in the bioadhesive delivery system is expected to stabilize the active drug from both chemical and physical degradation.

The phrase "oral disorders" or "dental disorders," relates to disorders of the lips, mouth and tongue including buccal mucosa, salivary glands, palate and stomatitis; dental caries including pulpits and periapical abscess; periodontal disease including gingivitis and periodontitis; temporomandibular joint disorders; neoplasms of tissue; and dental emergencies including toothache, fractured and avulsed teeth, and so forth.

The phrase "pharynx, esophageal and/or GI tract disorders" relates to those disorders found in the pharynx, esophagus, functional dyspepsia and from other nonspecific gastrointestinal complaints, gastrointestinal bleeding, disorders of the esophagus, stomach, and duodenum, acute abdomen and surgical gastroenterology, diarrhea and constipation, gastroenteritis, inflammatory diseases of the bowel and so forth.

Specific nonlimiting disorders that are treatable by the emulsions of this invention include the following:

Pre-esophageal dysphagia; esophageal dysphagia; gastroesophageal reflux; corrosive esophagitis and stricture such as a) esophageal diverticula b) hiatus hernia (or gastroesophageal reflux disease (GERD))

c) esophageal laceration and rupture, and d) infectious disorders of the esophagus; functional dyspepsia; nausea and vomiting; globus sensation; adult rumination; halitosis, real and imagined; arteriovenous malformations; gastritis; peptic ulcer; neoplasms of the stomach; abdominal pain; peritonitis; pancreatitis; cancer of the pancreas; diarrhea; constipation; gastroenteritis due to bacterial enterotoxins; menorrhagic colitis; staphylococcal food poisoning botulism; malabsorption syndromes such as i) carbohydrate intolerance
ii) celiac disease
iii) tropical spruce
iv) whipple's disease
v) intestinal lymphangiectasia and
vi) infection and infestation; Crohn's disease; ulcerative colitis and so forth.

Besides treating these various disorders, the delivery system is useful in enhancing the transport of biologically active components across the epithelium and into the capillary beds or circulatory structures within the epithelial mucosa. In this manner, biologically active material which would be rendered inactive by stomach acids or stomach/intestinal enzymes are able to be administered orally without need for injection. Examples of useful compounds that may be administered in this manner include proteins, peptides, polypeptides, hormones, and so forth. Non-limiting examples include the human growth hormone (hGH), insulin, tissue plasminogen activator (tPA), calcitonin, atrial natriuretic factor, and erythropoietin.

The present system is composed of two phases; a hydrophilic inner phase and a hydrophobic external phase. More particularly, the present system comprises a water-in-oil emulsion system having at least two phases, one phase comprises from about 25% to about 75% by volume of an internal hydrophilic phase, and preferably about 50% to about 70% by volume. The other phase comprises from about 25% to about 75% and preferably about 25% to about 50% by volume of an external hydrophobic phase. A unique feature of the external hydrophobic phase is that it is comprised of at least three components. One component being about 5% to about 50% by weight of the hydrophobic phase of an emulsifier. The second component being about 0% to about 75% by weight of a glyceride ester. The third component being about 10% to about 50% by weight of a wax material.

The hydrophilic polymer phase is present in the delivery system in amounts of about 25% to about 75% and most preferably about 50% to about 70% by volume of the overall system. As discussed above, the hydrophilic polymer phase is present in amounts at least equal to and preferably far greater than the external hydrophobic phase and is situated to enable the retention of active material, when used.

Preferably the hydrophilic phase is selected from the group consisting of water, glycerine, sorbitol solutions, sugar syrups, polymer solutions and mixtures thereof. The hydrophilic polymer material does not have to have any solubility in the hydrophobic phase and is preferably selected from water and sorbitol solutions, such as solutions containing 70% by weight sorbitol. A wide variety of natural polymers or derivatives thereof as well as synthetic polymers may also be used. Exemplary polymers include polyethylene glycol polymers having mean average molecular weight of at least 1000 and preferably from about 200 to 2 million or more. Exemplary sugar syrups include corn syrup, high fructose corn syrup and exemplary sugar solutions include cane sugar solutions, dextrose solutions, lycasin and so forth.

The hydrophobic phase is present in the delivery system in amounts generally less than the internal phase even though in some systems amounts to about are useable. In general amounts of about 25% to about 75% by volume of the system are useable with preferred amounts of about 25% to about 40% by volume being most preferred. The hydrophobic phase is specifically designed to avoid the prior use of low amounts of emulsifier and to produce a stable solid or semi-solid emulsion which becomes flowable at body temperature. In particular the present hydrophobic phase is composed of at least three essential components.

In general, the hydrophobic phase is composed of at least three components: a) an emulsifier, b) at least one glyceride ester and c) a wax material. By raising the emulsifier content in the external phase to be about or less than 50% of the hydrophobic phase, an adhesive formulation is prepared which will adhere to the mouth tissue and other mucosa, tissue and GI tract lining. The configuration of the external phase is critical to prevent the internal phase for coalescing and disintegrating after use. By using relatively high levels of emulsifiers, waxes and glyceride esters, the capability of the internal phase to absorb aqueous components is enhanced.

particularly preferred wax materials are selected from animal waxes, vegetable waxes, petroleum waxes, synthetic waxes, and mixtures thereof and include without limitation beeswax, candelilla wax, carnauba wax, microcrystalline wax and mixtures thereof. The wax materials are used in amounts of about 4% to 50% by weight. Also the wax has a preferred melting point within the range of about 50° to about 200° C.

The emulsifier used in the formulations of this invention find utility for preventing the internal phase from coalescing and disintegrating after use. It has the advantage of increasing the efficacy of any drug used over that obtainable with commercial formulations. Preferably, the emulsifiers are soluble in the hydrophobic (lipoidal) or external phase. Suitable emulsifiers are those oil miscible surface active compounds which are acceptable for use in foods, pharmaceuticals, and/or cosmetics. Examples of such emulsifiers are low molecular weight polyglycerols which have been esterified with fatty acids or fatty acid esters, or mono and diglyceride mixtures alone or with the addition of metallic soaps, such as, aluminum stearate. The metallic soaps appear to improve the characteristics of some of the emulsions.

Particularly preferred emulsifiers have a HLB value less than about 10 in order to obtain these desirable features. HLB is a qualitative description for emulsifiers wherein the ratio of hydrophile to lipophile can be assessed. Emulsifiers with HLB's below 10 are more lipid-soluble than water-soluble and tend to form stable water-in-oil emulsions.

The emulsifier is preferably selected from sorbitan esters, lecithin, 1 to 5 mole ethoxylates of fatty acids or esters, saccharide derivatives and mixtures thereof. particularly preferred emulsifiers are selected from the group consisting of soy lecithin, sorbitan monooleate, glycerol monooleate and mixtures thereof. Examples of saccharide derivatives include fatty acid saccharide derivatives such as sucrose oleate and sucrose stearate. The emulsifiers are present in the hydrophobic phase in amounts of about 5% to about 50% by weight of this phase and preferably in amounts of about 10% to about 30% by weight of this phase.

The glyceride esters are preferably selected from a blend of mono-, di-, and triglyceride esters of long chain fatty acids and most preferably fatty acids having straight or branched chain alkyls containing 10 to 32 carbon atoms. Specific examples of fatty acids include, lauric, myristic, palmitic, stearic, oleic, linoleic and linolenic acids. Combinations of glyceride esters are preferably used in the present formulations in order to produce products having the desired solid or semi-solid texture and stable emulsion properties. The glyceride esters are employed in amounts up to 75%, that is about 0% to about 75% of the hydrophobic phase. The glyceride esters also have preferred melting points between about 30° and about 50° C.

In addition to the noted component parts of the hydrophobic layer, this layer may also include other components to aid in the formation of the water-in-oil emulsions of this invention. Such components may include diluents as well as other excipients; binders such as ethylcellulose, sodium carboxymethyl cellulose, polyvinylpyrrolidone; and the like.

The formulations viscosities are prepared to have a solid to semi-solid consistency, that is they may range from being solid to having a semi-thick consistency. Solid emulsion formulations that liquify at body temperature are desirable where portability and ease of use by a patient are important. When using solid or semi-solid viscosities it is important that after the formulation is taken orally for it to start to exhibit a flow character to enable coating of the oral cavity, esophagus, pharynx and GI tract.

The overall degree of hardness, tack and melting point is controlled primarily by the blending of the external phase components, and to a lesser degree by the amount of dissolved species in the internal phase. A certain degree of plasticity is also required in the external phase, otherwise the finished product will crack and weep rather easily. Plasticity is usually achieved by incorporating appropriate amounts of lipid soluble oils and liquid surfactants. The main types of ingredients used to control the overall melting point and hardness are the hard fats (mostly triglycerides, but some mono and diglycerides), waxes (paraffin, microcrystalline, vegetable, mineral and animal), fatty alcohols and acids and fatty acid esters. These techniques are well known in formulating solids that melt at body temperatures.

The formulations of the invention may be used as is when preblended with an active material or drug when being prepared. While not being limited thereto, water-soluble drugs are preferably used in the hydrophilic internal phase whereas water-insoluble drugs are present in the external hydrophobic phase.

The active material(s) or drug(s) may be described as a single drug entity or a combination of entities. The delivery system is designed to be used with drugs having high water-solubility as well as with drugs having low water-solubility to produce a drug delivery system that has controlled release rates. The term "drug" includes without limitation, medicaments, vitamins, mineral supplements and other chemical or biological substances intended for use in the treatment, prevention, diagnosis, cure or mitigation of disease or illness of the oral cavity and gastrointestinal tract or substances which affect the structure of function of the oral cavity, esophagus and gastrointestinal tract body; all herein referred to as a "disorder."

Suitable categories of drugs that may be employed in the instant application may vary widely and generally represents any stable drug or combination thereof. Exemplary nonlimiting examples include:

Expanded Therapeutic Categories
Anabolic agents
Antacids
Anti-asthmatic agents
Anti-cholesterolemic and anti-lipid agents
Anti-coagulants
Anti-convulsants
Anti-diarrheals
Anti-emetics
Anti-infective agents
Anti-inflammatory agents
Anti-manic agents
Anti-nauseants
Anti-obesity agents
Anti-pyretic and analgesic agents
Anti-spasmodic agents.
Anti-thrombotic agents
Anti-uricemic agents
Antianginal agents
Antihistamines
Antitussives
Appetite suppressants
Biologicals Cerebral dilators
Coronary dilators
Decongestants
Diuretics
Erythropoietic agents
Expectorants
Gastrointestinal sedatives
Hyper-glycemic agents
Hypnotics
Hypo-glycemic agents
Ion exchange resins
Laxatives
Mineral supplements
Mucolytic agents
Neuromuscular drugs
Peripheral vasodilators
Psychotropics
Sedatives
Stimulants
Thyroid and anti-thyroid agents
Uterine relaxants Illustrative categories and specific examples include: (a) antitussives, such as dextromethorphan, dextromethorphan hydrobromide, noscapine, carbetapentane citrate, and chlophedianol hydrochloride; (b) antihistamines, such as chlorpheniramine maleate, phenindamine tartrate, pyrilamine maleate, doxylamine succinate, and phenyltoloxamine citrate; (c) decongestants, such as phenylephrine hydrochloride, phenylpropanolamine hydrochloride, pseudoephedrine hydrochloride, ephedrine; (d) various alkaloids, such as codeine phosphate, codeine sulfate and morphine; (e) mineral supplements such as potassium chloride, zinc chloride and calcium carbonates, magnesium oxide and other alkali metal and alkaline earth metal salts; (f) laxatives, vitamins and antacids (g) ion exchange resins such as cholestryramine; (h) anti-cholesterolemic and anti-lipid agents; (i) antiarrhythmics such as N-acetylprocainamide; (j) antipyretics and analgesics such as acetaminophen, aspirin and ibuprofen; (k) appetite suppressants such as phenylpropanolamine hydrochloride or caffeine; (l) expectorants such as guaifenesin; (m) antacids such as aluminum hydroxide and magnesium hydroxide; (n) biologicals such as peptides, polypeptides, proteins and amino acids, hormones, interferons and other bioactive peptididic compounds, such as hGH, tPA, calcitonin, ANF, EPO and insulin; and (o) anti-infective agents, such as antifungals, anti-virals, antiseptics and antibiotics.

The drugs are used in amounts that are therapeutically effective. While the effective amount of a drug will depend on the drug used, amounts of drug from about 5% to about 65% have been easily incorporated into the present delivery systems while achieving controlled release. Lesser amounts may be used to achieve efficacious levels of treatment for certain drugs.

The systems may be prepared by continuous or batch processes. As in preparing conventional emulsions, shear force is applied to the system components by use of homogenizers, mills, impingement surfaces, ultra-sound, shaking or vibration. Unlike conventional emulsions, the mixing shear should be at low levels in order to prevent destruction of the system by imparting excess energy. Temperature is not usually a critical factor in the preparation of the systems. The temperatures utilized will be dependent upon the final end product desired.

The systems may be prepared by mixing the internal with the external phase in a planetary-type mixer. Another manner of preparing the system is by use of a continuous mixer which comprises multiple impellers. The external phase is first introduced into the continuous mixer until it reaches the level of the lowest impeller in the mixing chamber. The two phases are then simultaneously introduced through the bottom of the mixer in proper proportion as its impeller or impellers rotate to apply a shear to the components. The finished product emerges through the top of the mixer and is stored or poured into molds and hardened. The actual speed of the impeller or impellers will vary, depending upon the product produced as will the rate of flow of the two phase streams.

In a preferred embodiment, the active agent or drug and ingredients of the internal phase were mixed together at room temperature (24° C.). The ingredients of the external phase were mixed together in a separate vessel. The internal phase composition was slowly added to the external phase composition as the two phases are mixed together at low shear until the desired viscosity was obtained.

It is believed that the release mechanism of active components may be a combination of several phenomena once the formulation is adhered to the oral cavity, esophagus and pharynx membrane walls and/or GI tract. Enzymatic degradation of the system, diffusion of the drug through the system, competitive adsorption, desorption of hydrophobic components from hydrophilic surface centers, convection of the drug through mesopores and macropores, diffusion of the external medium into the system by way of solubility or capillary action through porous structures created by the addition of hydrophilic polymers or water-soluble solids, as well as expansion of drug and/or system from water absorption into the inner phase.

The emulsion system may also be used in combination with one or more conventional excipients. The term "excipients" as used in the drug or food industry which do not alter the basic character and function of the active component or oral system and include flavors, sweetening agents and so forth.

The excipients are added to the oral delivery system anytime during processing. It should be recognized that certain excipients should be added prior to, during or after blending of the two phases.

Generally, the emulsion is prepared by separately making the hydrophilic and hydrophobic phases and then blending the phases together by adding the hydrophilic phase to the hydrophobic phase. In a particularly preferred procedure the hydrophobic phase is prepared by blending and melting the glyceride esters together with the wax material. Once a homogenous blend is obtained the emulsifier is added and blended to form the hydrophobic phase. The hydrophilic phase is then added in incremental amounts to the hydrophobic phase while mixing the components. As more and more of the aqueous phase is added the product begins to thicken to a smooth cream consistency. When the phase combination is complete, the product can be pumped, molded or filled into a final pharmaceutically acceptable carrier.

The emulsion once prepared may be stored for future use or formulated with conventional additives, that is pharmaceutically acceptable carriers, to prepare compositions which offer a variety of textures to suit particular applications. Such compositions may be in the form of a lozenge, tablet, toffee, nougat, chewy candy, oral hygiene preparations, breath fresheners and other oral applications and suspensions and so forth.

The pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

The preparation of confectionery and chewing gum products containing the present emulsions is also contemplated. When used in such systems, the formulations of this invention may be blended with the confectionery or chewing gum product, coated on the surface thereof or even center filled, to enable the active component to be administered.

As used herein, the term confectionery material means a product containing a bulking agent selected from a wide variety of materials such as sugar, corn syrup and in the case of sugarless bulking agents sugar alcohols such as sorbitol and mannitol and mixtures thereof. Confectionery material may include such exemplary substances as lozenges, tablets, toffee, nougat, chewy candy and so forth. In general, the bulking agent will comprise from about 5% to about 99% and preferably 20% to about 95% by weight of the medicated confectionery product.

Lozenges are flavored medicated dosage forms intended to be sucked and held in the mouth. They may be in the form of various shapes, the most common being flat, circular, octagonal and biconvex forms. The lozenge bases are generally in two forms, hard, boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having from 0.5% to about 1.5% moisture. Such materials normally contain up to about 92% corn syrup, up to about 70% sugar and from 0.1% to about 5.0% water. The syrup component generally is prepared from corn syrups high in dextrose, but may include other materials. Further ingredients such as flavorings, sweeteners, acidulents, colorants and so forth may also be added.

Boiled candy lozenges may also be prepared from non-fermentable sugars such as sorbitol, mannitol and hydrogenated corn syrup. The candy lozenges may contain up to about 95% sorbitol, a mixture of sorbitol and mannitol at a ratio of about 9.5 to 0.5 up to about 7.5 to 2.5 and hydrogenated corn syrup up to about 55% of the syrup component.

In contrast, compressed tablet lozenges contain particulate materials and are formed into structures under pressure. They generally contain sugars in amounts up to 95% and typical tablet excipients such as binders and lubricants as well as flavors, colorants and so forth.

The lozenges may be made of soft confectionery materials such as those contained in nougat. These materials contain two primary components, namely a high boiling syrup such as corn syrup or the like, and a relatively light textured frappé, generally prepared from gelatin, egg albumen, milk proteins such as casein, and vegetable proteins such as soy protein and the like. The frappé is generally relatively light, and may, for example, range in density from about 0.5 to about 0.7 g/cc.

By comparison, the high boiling syrup, or "bob syrup," is relatively viscous and possesses a higher density and frequently contains a substantial amount of sugar. Conventionally, the final nougat composition is prepared by the addition of the "bob syrup" to the frappé under agitation, to form the basic nougat mixture. Further ingredients such as flavorings, oils, additional sugar and the like may be added thereafter also under agitation. A general discussion of the composition and preparation of nougat confections may be found in B. W. Minifie, *CHOCOLATE, COCOA AND CONFECTIONERY: Science and Technology,* 2nd edition, AVI Publishing Co., Inc., Westport, Conn., (1980), at 15 pages 424–425, which discloses is incorporated herein by reference.

Unlike lozenges, nougat formulations are prepared by admixing the nougat candy base with the remaining ingredients, including active formulations of this invention, until a homogenous admixture is obtained and then forming the resulting mixture into suitable shapes for storage. The preparation of the nougat candy base may be achieved by routine procedures well known to the ordinary skilled artisan. One preferred procedure involves the preparation of a whipping component and blending with it a syrup component. See, for example, U.S. Pat. No. 4,683,138 to Glass et al.

The whipped component may be prepared by mixing the whipping agent with other desirable components. The whipped component is generally prepared from gelatin, egg albumen, milk proteins such as casein, and vegetable proteins such as soy protein, and the like which are added to a gelatin solution and rapidly mixed at ambient temperature to form an aerated sponge like mass.

The syrup component is prepared by initially mixing corn syrup, sugar component and an amount of water necessary to assure solution of the ingredients. The total water content is not critical, however, it is preferable to keep the initial water content below 40% by weight. This mixture is charged into a suitable cooker and cooked to a final water content of about 2% to about 11.0% by weight.

Once the above steps are complete, the whipped component and the syrup component may be combined, usually by the addition of whipped component to the syrup component after the syrup component's temperature has dropped to about 110° C. to about 188° C. The resultant combination is then mixed. At this point, an edible polyol may be added. If colorants are to be incorporated, they may be incorporated into the candy base at this point. The composition is then mixed until a uniform homogenous mass is formed.

The emulsions of this invention may then be added and mixed until a uniform homogenous mass is formed. If fats are to be incorporated, they are incorporated into the candy base at this time. The above composition is mixed until the temperature of the composition is less than about 90° C. but greater than 60° C. At this point, a graining compound, if employed, is added to the composition. If flavorings are to be incorporated, they may be added into the candy base also at this time. The mixture is then further mixed until uniform.

Once all of the reagents have been blended into the mixture, the mixture is allowed to cool. The mixture may be cooled to ambient temperatures before final forming operations are completed.

A variety of final forming techniques may be utilized, depending upon the shape and size of the final product as desired.

Once prepared the final composition may be processed into any desirable shape or form to render the product suitable for providing the necessary amount of mineral compound. Exemplary, non-limiting shapes include squares, rectangles, spheres, tabloids and biconvex shapes. Other suitable shapes may also be employed.

In the practice of this invention, a conventional chewing gum composition of the prior art may be used to assist in the delivery of the emulsions of this invention. The emulsions may be blended in the chewing gum composition, serve as a coating layer thereon or even be center-filled within the chewing gum composition.

Without being limited to specific chewing gum formulations, exemplary examples are described in U.S. Pat. Nos. 4,775,537 and 4,683,138. These formulations generally contain a gum base and modifiers to form an acceptable texture and sweetness.

The gum base compositions may contain conventional elastomer solvents to aid in softening the rubber component. Such elastomer solvents may comprise methyl, glycerol or pentaerythritol esters of rosins or modified rosins, such as hydrogenated, dimerized or polymerized rosins or mixtures thereof. Examples of elastomer solvents suitable for use herein include pentaerythritol ester of partially hydrogenated wood or gum rosin, pentaerythritol ester of wood or gum rosin, glycerol ester of partially dimerized rosin, glycerol ester of polymerized rosin, glycerol ester of tall oil rosin, glycerol ester of wood or gum rosin and partially hydrogenated wood or gum rosin, and partially hydrogenated methyl ester of rosin and mixtures thereof. The elastomer solvent may be employed in an amount ranging from about 10% to about 75% and preferably about 45% to about 70% by weight of the gum base.

A variety of traditional ingredients used as plasticizers or softeners such as lanolin, stearic acid, sodium stearate, potassium stearate, glycerol triacetate, glycerin, lecithin, and glycerol monostearate and the like, may also be incorporated into the gum base to obtain a variety of desirable textures and consistency properties. These additional materials are generally employed in amounts of up to about 30% by weight and preferably in amounts of from about 3% to about 5% by weight of the final gum base composition.

The chewing gum compositions may also employ sweetening agents (sweeteners). The sweetening agent may be selected from a wide range of materials including water-soluble sweetening agents, water-soluble artificial sweeteners, water-soluble sweetening agents derived from naturally occurring water-soluble sweeteners, dipeptide based sweeteners, and protein based sweeteners, including mixtures thereof.

The chewing gum compositions may additionally include effective amounts of the conventional additives of coloring agents such as titanium dioxide; emulsifiers such as lecithin and glycerol monostearate; maltodextrins; and fillers such as aluminum hydroxide, alumina, aluminum silicates, talc, dicalcium phosphate, calcium carbonate, and combinations thereof. Preferably the amount of fillers used is up to about 25% by weight of the gum base.

The chewing gum compositions may be produced by techniques well known to those skilled in the art. For example, using conventional equipment the gum base is heated to temperatures sufficiently high enough to soften the base without adversely effecting the physical and chemical make up of the base. The optimum temperatures utilized may vary depending on the composition of the gum base used, but such temperatures are readily determined by those skilled in the art without undue experimentation. For example, suitable temperature for softening the gum base are within the range of about 70° C. to about 90° C. Temperatures within the range of about 40° C. to about 60° C. may be used when the gum base used is amongst those disclosed in, for example, U.S. Pat. No. 4,587,125. During heating, the gum base is mixed with any of the optional components traditionally used with the gum base, such as plasticizers and elastomer solvents. In general, the order of addition of the various components (ingredients) of the chewing gum composition is not critical. The flavoring agents, however, should be added when the gum base has been allowed to cool to a temperature below the volatilization temperature of the flavoring agents used. The flavors may be added separately or blended together as a preblend before their addition. The mixture so produced is then extruded, using conventional equipment, and formed into suitable chewing gum shapes. The emulsions of this invention may also be added during the formation of the gum product or after it is formed either before or after the flavors are blended in the chewing gum composition.

Regarding center-filled gum, the emulsions of this invention may be pumped into the center-fill into a hollow-centered rope of chewing gum and then cut into pieces. The center-filled emulsion is then released upon chewing the gum composition resulting in release of the emulsion into the oral cavity.

Pharmaceutical emulsions or suspensions of this invention may also be prepared by conventional methods long established in the art of pharmaceutical compounding. The oral formulations may also contain conventional adjunct or excipient materials. Representative examples include the following materials:

(a) Preservatives such as benzoic acid, sorbic acid, methylparaben, propylparaben and ethylenediaminetetraacetic acid (EDTA). Preservatives are generally present in amounts up to about 1% and preferably from about 0.05% to about 0.5% by weight of the suspension;

(b) Buffers such as citric acid-sodium citrate, phosphoric acid-sodium phosphate, and acetic acidsodium acetate in amounts up to about 1% and preferably from about 0.05% to about 0.5% by weight of the suspension;

(c) Suspending agents or thickeners such as cellulosics like methylcellulose, carageenans like alginic acid and its derivatives, xanthin gums, gelatin, acacia, and microcrystalline cellulose in amounts up to about 20% and preferably from about 1% to about 15% by weight of the suspension;

(d) Antifoaming agents such as dimethyl polysiloxane in amounts up to about 0.2% and preferably from about 0.01% to about 0.1% by weight of the suspension;

(e) Sweeteners include those sweeteners both natural and artificial well known in the art;

(f) Flavorants include both natural and artificial flavors, and mints such as peppermint, menthol, vanilla, artificial vanilla, chocolate, artificial chocolate, cinnamon, various fruit flavors, both individual and mixed may be utilized in amounts from about 0.5% to about 5% by weight of the suspension;

(g) Colorants useful in the presentation invention include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, and known as F.D.&C. dyes and the like. Such dyes are generally present in amounts up to about 0.25% and preferably from about 0.05% to about 0.2% by weight of the suspension;

(h) Decolorizing agents such as sodium metabisulfite, ascorbic acid and the like may be incorporated into the suspension to prevent color changes due to aging. In general, amounts up to about 0.25% and preferably 0.5% to 0.2% by weight of the suspension are used; and (i) Solubilizers such as alcohol, propylene glycol, polyethylene glycol and the like may be us ed to solubilize the flavors. Solubilizing agents a re generally present in amounts up to 10%; preferably from about 2% to about 5% by weight of the suspension.

Pharmaceutical tablets of this invention may also be in chewable form. This form is particularly advantageous because of convenience and patient acceptance. To achieve acceptable stability and quality as well as good taste and mouth feel several considerations are important, namely amount of active substance per tablet, flavor, compressibility and organoleptic properties of the drug.

The formulations may also be formulated with conventional well known ingredients to form lip balm or components of lipstick to aid in delivery of the active component present in the emulsion.

The following examples are illustrative of preferred embodiments of the invention and are not to be construed as limiting the invention thereto. All percentages of the two phases are based on volume % whereas percentages of phase components are based on the percent by weight of the phase unless otherwise indicated and all totals equal 100% by weight.

EXAMPLE 1

This example describes the preparation of a solid stable oral pharmaceutical preparation.

| Formulation Components | Weight % |
| --- | --- |
| Mineral Oil | 1.9 |
| Di and triglyceride esters having melting point 33.5–35.5° C. | 7.1 |
| Mono-, Di-, and triglyceride esters having melting point 33.5–35.5° C. | 7.1 |
| Triglyceride esters having melting point 42–44° C. | 3.67 |
| Microcrystalline wax | 0.92 |
| Beeswax | 4.55 |
| Sorbitan monooleate | 6.83 |
| Glycerol Monooleate | 0.83 |
| Soy Lecithin | 2.5 |
| Flavor | 0.3 |
| Methyl and propyl parabens | .03 |
| Water | 61.89 |
| Sorbitol 70% Solution | 2.38 |

Procedure
1) Water and Sorbitol solution are weighed into a suitable container and stirred until uniform and then warmed to 50°–55° C.
2) In a separate container the glyceride esters were melted with the beeswax and mineral oil. Beeswax melts at 89° C., however in the presence of the other components it can incorporate itself into the mixture at a lower temperature.
3) Once the components of step 2 are melted, add the parabens and microcrystalline wax. Heat to at least 65° C. to melt beeswax. Once the wax is melted uniformly, allow blend to cool to 50°–55° C.
4) To the melt of step 3 add the following in order making sure each is dissolved or evenly mixed before adding the next component. Soy lecithin, glycerol monooleate and sorbitan monooleate. When complete adjust temperature to 50°–55° C.
5) Immediately before the combination of the hydrophobic phase and water phases add the flavor to the phase it is most soluble in.
6) With moderate stirring add the aqueous phase to the wax phase slowly. Maintain 50°–55° C. temperature throughout this operation. As more and more of the aqueous phase is added the product should begin to thicken to a smooth cream.
7) When phase combination is complete and the temperature is 50°–55°C. the product can be pumped, molded or filled into the final product form, then allowed to cool and become hard.

The product when mixed with various drugs and taken orally, adhered to the oral mucosa and esophageal mucosa. The product remained in place for from 30 minutes to 24 hours. In this time period, sufficient active ingredient diffused from the substrate through the oral and esophageal epithelium and into the vasculature to obtain efficacious levels of the drug.

EXAMPLE 2

This example describes the preparation of a solid, cough suppressant lozenge.

| Formulation Components | Weight % |
| --- | --- |
| Water | 64.609 |
| Fructose | 3.544 |
| Sodium Saccharin | 0.162 |
| Medium chain triglyceride oil | 1.789 |
| Di and triglyceride esters having a melting point of 33.5–35.5 deg. C. | 5.176 |
| Mono-, di- and triglyceride esters having a melting point of 33.5–35.5 deg. C. | 5.176 |
| Triglyceride esters having a melting point of 42–44 deg. C. | 7.139 |
| Microcrystalline wax | 0.894 |
| Methyl and propylparabens | 0.136 |
| Beeswax | 4.418 |
| Sorbitan Monooleate | 0.809 |
| Distilled monoglyceride | 0.809 |
| Soy Lecithin | 2.427 |
| Menthol/Eucalyptus flavor | 2.912 |
| Total: | 100.000 |

Procedure:
1) The water, fructose and sodium saccharin were weighed into a suitable container, stirred until the solids were dissolved then warmed to 50–55 deg. C.
2) The medium chain triglyceride oil, glyceride esters and microcrystalline wax were weighed into a separate container and warmed to 90 deg. C to melt the solid components.
3) The soy lecithin was added to the container from Step 2 and stirred until dissolved at a temperature of 90 deg. C.
4) The temperature of the solution was allowed to begin cooling down to 50–55 deg. C. The methylparaben, propylparaben and beeswax were added to the container from Step 3 and stirred until dissolved.
5) The sorbitan monooleate and distilled monoglyceride were added to the container from Step 4 and stirred until dissolved.
6) At a temperature of 50–55 deg. C. one third of the flavor was added to the container and stirred.
7) With moderate stirring the aqueous phase was slowly added to the oil phase. The temperature was maintained at 50–55 deg. C. throughout this operation. As more and more of the aqueous phase was added the product began to thicken to a smooth cream.
8) When the phase combination was complete, the remaining two thirds of the flavor was added and stirred until uniformly distributed.
9) At a temperature of 50–55 deg. C. the product can be pumped molded or filled into the final product form then allowed to cool and become hard.

EXAMPLE 3

The oral preparation of Example 1 can be used with human growth hormone wherein the hormone is added to the inner phase (Step 1) in amounts of about 0.01% to about 2.0% by weight. Human growth hormone is a single polypeptide chain of 191 amino acids having a molecular weight of 22,124, having the empirical formulation of $C_{990} H_{1529} N_{263} O_{299} S_7$, also known as hGH, somatotropin and human growth hormone. When consumed orally, the preparation would be expected to adhere to the oral and esophageal mucosa for 2 to 8 hours with diffusion of the drug being completed within the first two hours of use.

EXAMPLE 4

The procedure of Example 3 can be repeated with 0.01% to 2.0% tissue plasminogen activator. tPA, also known as fibrinokinase, molecular weight approximately 70,000, described as a peptiditic human therapeutic agent used to prevent the formation of fibrin clots or dissolve fibrin clots. When consumed orally, the preparation would be expected to adhere to the oral and esophageal mucosa for 2 to 8 hours with diffusion of the drug being completed within the first two hours of use.

EXAMPLE 5

The procedure of Example 3 can be repeated with 0.00001% to 0.1% calcitonin added to the emulsion system. Calcitonin, also known as thyrocalcitonin, or TCA, molecular weight approximately 4,500, is a naturally occurring hormone secreted from mammalian thyroid gland. When consumed orally, the preparation would be expected to adhere to the oral and esophageal mucosa for 2 to 8 hours with diffusion of the drug being completed within the first two hours of use.

EXAMPLE 6

The procedure of Example 3 can be repeated with 0.0001% to 0.1% ANF added to the emulsion system. Atrial natriuretic factor, also known as atriopeptin, or ANF, is a potent peptide or mixture of homologous peptides derived from the atrium of mammalian heart and is involved in the hormonal regulation of fluid volume and blood pressure. ANF is composed of 21–33 specific amino acids having a molecular weight of approximately 4,000. When consumed orally the preparation would be expected to adhere to the oral and esophageal mucosa for 2 to 8 hours with diffusion of the drug being completed within the first two hours of use.

EXAMPLE 7

The procedure of Example 3 can be repeated with 0.001% to 0.1% Erythropoietin added to the emulsion system. Erythropoietin, also known as erythropoiesis stimulating factor, EPO, or epogen, is a glycoprotein which stimulates red blood cell formation, produced mainly in the kidneys of mammals, and has been recently produced by genetic engineering. When consumed orally, the preparation would be expected to adhere to the oral and esophageal mucosa for 2 to 8 hours with diffusion of the drug being completed within the first two hours of use.

The invention being thus described, it will be obvious that the same may be varied in many ways. Such variations are not to be regarded as a departure from the spirit and scope of the invention and all such modifications are intended to be included within the scope of the following claims.

What is claimed is:

1. A solid or semi-solid bioadherent, orally ingestible system, which comprises: a water-in-oil system having at least two phases, one phase comprises from about 25% to about 75% by volume of an internal hydrophilic phase wherein the hydrophilic phase is selected from the group consisting of water, glycerine, sorbitol solutions, sugar syrups, polymer solutions and mixtures thereof, and the other phase comprises from about 25% to about 75% by volume of an external hydrophobic phase, wherein the external hydrophobic phase is comprised of three components, a) one component being about 5% to about 50% of an emulsifier, b) a second component being about 10% to about 75% of a mixture of glyceride esters of long chain fatty acids and c) a third component being about 10% to about 50% of a wax material.

2. The ingestible system of claim 1, wherein the hydrophilic phase contains an active pharmaceutical material.

3. The ingestible system of claim 2, wherein the active pharmaceutical material is water-soluble.

4. The ingestible system of claim 1, wherein the internal phase is present in amounts of about 50% to about 70% by volume.

5. The ingestible system of claim 1, wherein the external phase contains an active pharmaceutical material.

6. The ingestible system of claim 5, wherein the active pharmaceutical material is water-insoluble.

7. The ingestible system of claim 1, wherein the glyceride esters are selected from the group consisting of mono-, di-, and tri-glyceride esters of long chain fatty acids having from 12 to 32 carbon atoms.

8. The ingestible system of claim 1, wherein the emulsifier present in the hydrophobic phase is selected from the group consisting of sorbitan esters, lecithin, 1 to 5 mole ethoxylates of fatty acids or alcohols, saccharides derivatives and mixtures thereof.

9. The ingestible system of claim 1, wherein the emulsifier is selected from the group consisting of soy lecithin, sorbitan monooleate and mixtures thereof.

10. The ingestible system of claim 1, wherein the external phase is present in amounts of about 25% to about 40% by volume of the entire system.

11. The ingestible system of claim 1, wherein the wax material is selected from the group consisting of animal waxes, vegetable waxes, synthetic waxes and mixtures thereof.

12. A method for treating an oral or esophageal disorder or absorption of an active material for its systemic effect, which comprises: administering orally a therapeutically effective amount of a solid or semi-solid bioadherent, orally ingestible system, which comprises: a water-in-oil system having at least two phases, one phase comprises from about 25% to about 75% by volume of an internal hydrophilic phase wherein the hydrophilic phase is selected from the group consisting of water, glycerine, sorbitol solutions, sugar syrups, polymer solutions and mixtures thereof, and the other phase comprises from about 25% to about 75% by volume of an external hydrophobic phase, and wherein the external hydrophobic phase comprises three components, a) one component being about 5% to about 50% of an emulsifier, b) a second component being about 0% to about 75% of a mixture of glyceride esters of long chain fatty acids and c) a third component being about 10% to about 50% of a wax material.

13. The method of claim 12, wherein the hydrophilic phase contains an active pharmaceutical material.

14. The method of claim 13, wherein the active pharmaceutical material is water-insoluble.

15. The method of claim 12, wherein the hydrophilic phase is selected from the group consisting of water, glycerine, sorbitol solutions, sugar syrups, polymer solutions and mixtures thereof.

16. The method of claim 12, wherein the internal phase is present in amounts of about 50% to about 70% by volume.

17. The method of claim 12, wherein the glyceride esters are selected from the group consisting of mono-, di-, and tri-glyceride esters of long chain fatty acids having from 12 to 32 carbon atoms.

18. The method of claim 12, wherein the emulsifier present in the hydrophobic phase is selected from the group consisting of sorbitan esters, lecithin, 1 to 5 mole ethoxylates of fatty acids or alcohols, saccharides derivatives and mixtures thereof.

19. The method of claim 18, wherein the emulsifier is selected from the group consisting of soy lecithin, sorbitan monooleate and mixtures thereof.

20. The method of claim 12, wherein the ingestible system adheres to the oral mucosa and esophageal mucosa for 30 minutes to 24 hours.

21. The method of claim 12, wherein the ingestibte system adheres to the oral mucosa and esophageal mucosa for 2 to 8 hours.

22. A medicated chewing gum composition, which comprises:
   a) a gum base in an amount sufficient to form a chewing gum composition;
   b) effective amounts of chewing gum additives to soften the gum base; and
   c) an effective amount of an active pharmaceutical composition dispersed within a water-in-oil emulsion system having at least two phases, one phase comprises from about 25% to about 75% by volume of an internal hydrophilic phase wherein the hydrophilic phase is selected from the group consisting of water, glycerine, sorbitol solutions, sugar syrups, polymer solutions and mixtures thereof, and the other phase comprises from about 25% to about 75% by volume of an external hydrophobic phase, wherein the external hydrophobic phase is comprised of three components, a) one component being about 5% to about 50% of an emulsifier, b) a second component being about 10% to about 75% of a mixture of glyceride esters of long chain fatty acids and c) a third component being about 10% to about 50% of a wax material.

23. The chewing gum composition of claim 22 wherein the hydrophilic phase contains an active pharmaceutical material.

24. The chewing gum composition of claim 22, wherein the active pharmaceutical material is water-soluble.

25. The chewing gum composition of claim 22, wherein the internal phase is present in amounts of about 50% to about 70% by volume.

26. The chewing gum composition of claim 22, wherein the external phase contains an active pharmaceutical material.

27. The chewing gum composition of claim 22, wherein the active pharmaceutical material is water-insoluble.

28. The chewing gum composition of claim 22, wherein the external phase is present in amounts of about 25% to about 40% by volume of the entire system.

29. The chewing gum composition of claim 22, wherein the internal phase of the emulsion is present in amounts of about 50% to about 70% by volume.

30. The chewing gum composition of claim 22, wherein the active pharmaceutical composition dispersed within the emulsion is coating on the surface of the chewing gum composition.

31. The chewing gum composition of claim 22, wherein the active pharmaceutical composition dispersed within the emulsion is center-filled within the chewing gum composition.

32. The chewing gum composition of claim 22, wherein the active pharmaceutical composition dispersed within the emulsion is homogeneously mixed throughout the chewing gum composition.

33. A medicated confectionery composition, which comprises:
   a) a confectionery composition; and
   b) an effective amount of an active pharmaceutical composition dispersed within a water-in-oil emulsion system having at least two phases, one phase comprises from about 25% to about 75% by volume of an internal hydrophilic phase wherein the hydrophilic phase is selected from the group consisting of water, glycerine, sorbitol solutions, sugar syrups, polymer solutions and mixtures thereof, and the other phase comprises from about 25% to about 75% by volume of an external hydrophobic phase, wherein the external hydrophobic phase is comprised of three components, a) one component being about 5% to about 50% of an emulsifier, b) a second component being about 10% to about 75% of a mixture of glyceride esters of long chain fatty acids and c) a third component being about 10% to about 50% of a wax material.

34. The confectionery composition of claim 33, wherein the hydrophilic phase contains an active pharmaceutical material.

35. The confectionery composition of claim 34, wherein the active pharmaceutical material is water-soluble.

36. The confectionery composition of claim 33, wherein the internal phase is present in amounts of about 50% to about 70% by volume.

37. The confectionery composition of claim 33, wherein the external phase contains an active pharmaceutical material.

38. The confectionery composition of claim 37, wherein the active pharmaceutical material is water-soluble.

39. The confectionery composition of claim 33, wherein the external phase is present in amounts of about 25% to about 40% by volume of the entire system.

40. The confectionery composition of claim 33 wherein the internal phase of the emulsion is present in amounts of about 50% to about 70% by volume.

41. The confectionery composition of claim 33, wherein the active pharmaceutical composition dispersed within the emulsion is coating on the surface of the confectionery composition.

42. The confectionery composition of claim 33, wherein the active pharmaceutical composition dispersed within the emulsion is center-filled within the confectionery composition.

43. The confectionery composition of claim 33, wherein the active pharmaceutical composition dispersed within the emulsion is homogeneously mixed throughout the confectionery composition.

* * * * *

UNITED STATES PATENT AND TRADEMARK OFFICE
CERTIFICATE OF CORRECTION

PATENT NO. : 5,554,380
DATED : September 10, 1996
INVENTOR(S) : Robert Cuca, et. al.

It is certified that error appears in the above-indentified patent and that said Letters Patent is hereby corrected as shown below:

Column 3, line 62, change "10°" to -- 10% --.

Column 3, line 63, change "50°" to -- 50% --.

Column 4, line 10, change "10" to -- 10% --.

Column 4, line 12, change "10°" to -- 10% --.

Column 4, line 12, change "50°" to -- 50% --.

Column 6, line 54, after "about" and before "are", insert -- 75% --.

Column 7, line 3, change "for" to -- from --.

Column 7, line 8, change "particularly" to -- Particularly --.

Column 14, line 60, change "us ed" to -- used -- .

Column 14, line 61, change "a re" to -- are --.

Signed and Sealed this

Fourteenth Day of January, 1997

Attest:

BRUCE LEHMAN

*Attesting Officer*   *Commissioner of Patents and Trademarks*